United States Patent [19]
Froix et al.

[11] Patent Number: 5,851,538
[45] Date of Patent: Dec. 22, 1998

[54] RETINOID FORMULATIONS IN POROUS MICROSPHERES FOR REDUCED IRRITATION AND ENHANCED STABILITY

[75] Inventors: Michael Froix, Mountain View; Masha Pukshansky, San Francisco; Sergio Nacht, Redwood City, all of Calif.

[73] Assignee: Advanced Polymer Systems, Inc., Redwood City, Calif.

[21] Appl. No.: 581,126

[22] Filed: Dec. 29, 1995

[51] Int. Cl.$^6$ ................ A61K 7/00; A61K 7/02
[52] U.S. Cl. ............. 424/401; 424/78.02; 424/78.03; 514/844; 514/938
[58] Field of Search .................. 424/78.02, 401, 424/489, 780.03; 514/938, 844

[56] References Cited

U.S. PATENT DOCUMENTS

| | | | |
|---|---|---|---|
| 3,906,108 | 9/1975 | Felty | 424/318 |
| 4,247,547 | 1/1981 | Marks | 424/240 |
| 4,603,146 | 7/1986 | Kligman | 514/559 |
| 4,826,828 | 5/1989 | Wilmott et al. | 514/63 |
| 4,877,805 | 10/1989 | Kligman | 514/381 |
| 5,073,365 | 12/1991 | Katz et al. | 424/489 |
| 5,135,740 | 8/1992 | Katz et al. | 424/401 |
| 5,145,675 | 9/1992 | Won | 424/78.31 |
| 5,156,843 | 10/1992 | Leong et al. | 424/411 |
| 5,484,816 | 1/1996 | Yanagida et al. | 514/725 |

FOREIGN PATENT DOCUMENTS

| | | |
|---|---|---|
| 0 316 054 | 5/1989 | European Pat. Off. . |
| WO 91/04732 | 10/1989 | European Pat. Off. ......... A61K 9/16 |
| 0 369 741 | 5/1990 | European Pat. Off. . |
| 0 440 398 A1 | 1/1991 | European Pat. Off. ......... A61K 7/48 |
| 0 586 106 A1 | 8/1993 | European Pat. Off. ......... A61K 7/00 |
| 2 666 015 | 2/1992 | France . |
| WO 93/00085 | 6/1991 | WIPO .......................... A61K 31/215 |

OTHER PUBLICATIONS

B. Rössler et al., "Effect of collagen microparticles on the stability of retinol and its absorption into hairless mouse skin in vitro", *Pharmazie*, 49(2/3), 175–179 (1994).

*Chem. Abs.*, 121(6), 65491x (1994); abstract of S. Torrado et al., "Microencapsulation of vitamin A", *An. R. Acad. Farm.*, 59(1), 109–119 (1994).

*Primary Examiner*—Thurman K. Page
*Assistant Examiner*—James M. Spear
*Attorney, Agent, or Firm*—Heller Ehrman White & McAuliffe

[57] ABSTRACT

Retinoids for topical skin application are formulated as impregnants in porous microspheres. Thus formulated, the retinoids display a surprisingly high level of stability and low degree of skin irritation.

16 Claims, No Drawings

_5,851,538_

RETINOID FORMULATIONS IN POROUS MICROSPHERES FOR REDUCED IRRITATION AND ENHANCED STABILITY

BACKGROUND OF THE INVENTION

Retinoic acid and its various analogs and derivatives, known collectively as retinoids, have been enjoying increasing popularity as active ingredients in skin care compositions, primarily for acne, photoaging and sun damage. A problem associated with cosmetic and therapeutic formulations of retinoids is the tendency of these compounds to decompose upon exposure to such factors as heat, light, oxygen and trace amounts of metal ions. In addition, retinoids tend to cause skin irritation.

The decomposition problem is addressed to some extent by formulating retinoids to include antioxidants and chelating agents. These have been of limited success, however, particularly in oil-in-water emulsions, which are generally the formulations of choice for skin care products. Oil-in-water emulsions appear to facilitate the diffusion of oxygen to the retinoids, thereby lessening the stabilizing effect of the anitoxidants.

Reversal of the phases to form water-in-oil emulsions has been proposed as a means to improve stability. Disclosures of emulsions of this type appear in PCT International Publication No. WO 93/00085 (Johnson and Johnson Consumer Products, Inc., publication date Jan. 7, 1993), European Patent Publication No. 440398 (Johnson and Johnson Consumer Products, Inc., publication date Aug. 7, 1991), and European Patent Publication No. 586106 (Johnson and Johnson Consumer Products, Inc., publication date Mar. 9, 1994). Water-in-oil emulsions however are greasy and not aesthetically acceptable. In addition, they do not lessen the skin irritation caused by the retinoids.

A retinoid formulation with an aqueous continuous phase which resists decomposition and entails a reduced degree of skin irritation is therefore needed. The present invention addresses this need.

SUMMARY OF THE INVENTION

It has now been discovered that skin irritation due to retinoids can be reduced and stability can be increased by formulating the retinoids as particles or particle suspensions in which the particles are porous matrices with the retinoid retained inside the pores. The particles are solid, water-insoluble particles, microscopic in size, with a continuous network of pores open to the exterior of the particles, and the particle material is chemically inert with respect to the retinoids and any other ingredients such as chelating agents, antioxidants, and surface-active agents, and further with respect to the conventional ingredients frequently included in aqueous phases of oil-in-water emulsions. The retinoids are not part of the particle matrix, but reside solely in the pores, in which the retinoids are typically deposited by conventional physical means subsequent to the formation of the particles.

A preferred formulation in accordance with this invention is one in which the retinoid-impregnated particles are dispersed in an aqueous suspension medium, particularly a medium which also contains adjuvants and other ingredients that are typical of aqueous emulsions formulated for topical application to the skin. Further preferred formulations are those which include one or more antioxidants, one or more chelating agents or both, particularly in a mixture with the retinoid and residing as such with the retinoid in the pores of the particles.

These and other features, preferred embodiments, and advantages of the invention will be apparent from the description that follows.

DETAILED DESCRIPTION OF THE INVENTION AND PREFERRED EMBODIMENTS

The term "retinoid compound" is used in this specification to denote both naturally occurring and synthetic compounds bearing the general structure of vitamin A (retinol) and variations on that structure which bear similarities to retinol in terms of biological activity. Included among this class are:
retinol: 3,7-dimethyl-9-(2,6,6-trimethyl-1-cyclohexen-1-yl)-2,4,6,8-nonatetraen-1-ol (all trans)
retinyl palmitate
retinyl acetate
retinyl linoleate
dehydroretinol: 3,7-dimethyl-9-(2,6,6-trimethyl-1,3-cyclohexadien-1-yl)-2,4,6,8-nonatetraen-1-ol
retinal (aldehyde form of retinol)
13-cis-retinoic acid
etretinate: (all-E)-9-(4-methoxy-2,3,6-trimethylphenyl)-3,7-dimethyl-2,4,6,8-nonatetraenoic acid ethyl ester
etretin: (all-E)-9-(4-methoxy-2,3,6-trimethylphenyl)-3,7-dimethyl-2,4,6,8-nonatetraenoic acid
motretinide: N-ethyl-9-(4-methoxy-2,3,6-trimethylphenyl)-3,7-dimethylnona-2,4,6,8-tetraen-1-oic acid ethyl amide
(E,E)-9-(2,6-dichloro-4-methylphenyl)-3,7-dimethyl-2,4,6,8-tetraen-1-oic acid ethyl ester
(E,E)-4-[2-methyl-4-(2,6,6-trimethyl-1-cyclohexen-1-yl)-1,3-butadienyl]benzoic acid
(E)-4-[4-methyl-6-(2,6,6-trimethyl-1-cyclohexen-1-yl)-1,3,5-hexatrienyl]benzoic acid
(all-E)-3,7-dimethyl-9-(3-thienyl)-2,4,6,8-nonatetraenoic acid
(E,E,E)-3-methyl-7-(5,6,7,8-tetrahydro-5,5,8,8,-tetramethyl-2-naphthalenyl)-2,4,6-octatrienoic acid
(E,E)-6-[2,6,6-trimethyl-1-cyclohexen-1-yl)ethenyl]-2-naphthalenecarboxylic acid
(E,E,E)-7-(2,3-dihydro-1,1,3,3-tetramethyl-1H-inden-5-yl)-3-methyl-2,4,6-octatrienoic acid
(E)-4-[2-(2,3-dihydro-1,1,3,3-tetramethyl-1H-inden-5-yl)-1-propenyl]benzoic acid
(E)-4-[2-(5,6,7,8-tetrahydro-5,5,8,8-tetramethyl-2-naphthalenyl)-1-propenyl]benzoic acid
(E)-4-[2-(5,6,7,8-tetrahydro-3-methyl-5,5,8,8-tetramethyl-2-naphthalenyl)-1-propenyl]benzoic acid
(E)-1,2,3,4-tetrahydro-3-methyl-1,1,4,4-tetramethyl-6-(1-methyl-2-phenylethenyl)naphthalene
(E)-1,2,3,4-tetrahydro-1,1,4,4-tetramethyl-6-naphthyl-2-naphthalenecarboxylic acid
(E)-6-{2-[4-(ethylsulfonyl)phenyl]-1-methylethenyl}-1,2,3,4-tetrahydro-1,1,4,4-tetramethylnaphthalene-4-[(5,6,7,8-tetrahydro-5,5,8,8-tetramethyl-2-naphthalenyl)ethynyl]benzoic acid
(E)-2-(1,1,4,4-tetramethyl-1,2,3,4-tetrahydronaphth-7-yl)-1-[4-(tetrazol-5-yl)phenyl]-1-propene
(E)-4-[2-(5,6,7,8-tetrahydro-7-hydroxy-5,5,8,8-tetramethyl-2-naphthalenyl)-1-propenyl]benzyl alcohol
Preferred retinoids are retinol, retinal, retinoic acid, retinyl palmitate, retinyl acetate, and retinyl linoleate. More preferred are retinol, retinal, retinyl palmitate, retinyl acetate, and retinyl linoleate, and the most preferred is retinol.

The retinoid compound is preferably combined with additional ingredients to form a retinoid composition which is deposited in the pores of the particles. The quantity of the retinoid compound in the retinoid composition is not critical and can vary widely. In most applications, a retinoid composition containing from about 1% to about 90% by weight of the retinoid compound, preferably from about 5% to about 75%, and most preferably from about 5% to about 60%, will provide the best results. The additional ingredients are included to further enhance the stability and usefulness of the retinoid compound.

One type of additional ingredient is an antioxidant. Both water-soluble and oil-soluble antioxidants may be used. Examples of water-soluble antioxidants are ascorbic acid (vitamin C), isoascorbic acid, imidazoline urea, methyl paraben, sodium sulfite, sodium metabisulfite, sodium bisulfite, sodium thiosulfite, sodium formaldehyde sulfoxylate, thioglycerol, thiosorbitol, thiourea, thioglycolic acid, cysteine hydrochloride, and 1,4-diazabicyclo-(2,2,2)-octane. Examples of oil-soluble antioxidants are butylated hydroxytoluene (BHT), butylated hydroanisole (BHA), $\alpha$-tocopherol (vitamin E), ascorbyl palmitate, phenyl-$\alpha$-naphthylamine, hydroquinone, propyl gallate, and nordihydroguiaretic acid. The amount of antioxidant can vary and is not critical to this invention. In most applications, however, an amount ranging from about 0.001% to about 75% by weight of the retinoid composition will provide best results.

A second type of additional ingredient is a chelating agent to serve as a scavenger for trace metals. Examples of chelating agents suitable for use in this invention are ethylenediamine tetraacetic acid (EDTA) and derivatives and salts of EDTA, dihydroxyethylglycine, citric acid, and tartaric acid. The amount of chelating agent can likewise vary and is not critical to this invention. In most applications, an amount ranging from about 0.01 to about 1.0% by weight of the retinoid composition will provide best results.

When the particles are dispersed in an aqueous medium, the aqueous medium can also contain antioxidants, chelating agents or both.

Further substances as optional additional ingredients for the retinoid composition, the aqueous suspending medium or both include surfactants, humectants, perfume oils, sunscreens, and other therapeutic or cosmetic substances. Anionic, cationic and nonionic surfactants can be used. Examples are polysorbates and polyoxyalkylene esters, such as polysorbate 20, polysorbate 80, polyoxyethylene 25 oxypropylene stearate, polyoxyl 40 stearate, polyethyleneglycol 400 monostearate, and polyethyleneglycol 600 monostearate. Examples of the other optional ingredients will be readily apparent to those skilled in the art.

The solid porous particles in whose pores the retinoid compositions are retained may be rigid or resiliently compressible, but in either case are solid and water-insoluble. The particles contain a network of interconnected pores open to the particle surface, providing substantially full communication between the internal pore space and the particle exterior. Particles of this type are disclosed by Won, in U.S. Pat. No. 4,690,825; Won, U.S. Pat. No. 5,145,675; Katz et al., U.S. Pat. No. 5,073,365; Katz et al., U.S. Pat. No. 5,135,740; and Jankower et al., U.S. Pat. No. 4,873,091. The disclosures of these patents are incorporated herein by reference.

The particles are frequently spherical in shape, most often ranging from about one to about 500 microns in diameter, particularly from about 5 to about 100 microns. The pore dimensions within the particles may also vary, with optimum dimensions depending on the chemical characteristics of the polymers used to form the particles as well as the diffusive characteristics of the retinol ester retained inside. In general, best results are obtained with total pore volumes ranging from about 0.01 to about 4.0 cc/g, preferably from about 0.1 to about 2.0 cc/g; surface areas ranging from about 1 to about 500 $m^2/g$, preferably from about 20 to about 350 $m^2/g$; and average pore diameters ranging from about 0.0001 to about 3.0 micron, preferably from about 0.003 to about 1.0 micron. Optimal parameters for a methyl methacrylate/ethyleneglycol dimethacrylate particle are a pore volume within the range of 0.72 to 0.95 cc/g, a surface area within the range of 150 to 360 $m^2/g$, a monomer content of less than 75 ppm, a solvent content of less than 50 ppm, a moisture content of less than 1% (weight basis), a mean (weight average) particle diameter of 5 to 30 microns, and a particle size distribution such that 90% (weight basis) of the particles are less than 45 microns in diameter.

The particles are generally organic polymers, formed by suspension polymerization, as described in the patents referenced above. Monoethylenically unsaturated monomers suitable for preparing the particles include ethylene, propylene, isobutylene, diisobutylene, styrene, ethylvinylbenzene, vinyltoluene and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, ethoxyphenyl, ethoxybenzyl and ethoxycyclohexyl esters; vinyl esters, including vinyl acetate, vinyl propionate and vinyl laurate; vinyl ketones, including vinyl methyl ketone, vinylisopropyl ketone and methyl isopropenyl ketone; and vinyl ethers, including vinyl methyl ether, vinyl ethyl ether and vinyl isobutyl ether.

Polyethylenically unsaturated crosslinking monomers suitable for use in the particles include diallyl phthalate, ethylene glycol diacrylate, ethylene glycol dimethacrylate, polyethylene glycol diacrylate, polyethylene glycol dimethacrylate, trimethylolpropanetrimethacrylate and divinylsulfone; polyvinyl and polyallyl ethers of ethylene glycol, of pentaerythritol, of diethyleneglycol and of resorcinol, divinylketone, divinylsulfide, allyl acrylate, diallyl maleate, diallyl fumarate, diallyl succinate, diallyl adipate, diallyl sebacate, divinyl sebacate, diallyl tartrate, and diallyl silicate.

Particularly preferred particles for use in the present invention are those formed by the copolymerization of styrene and divinylbenzene, vinyl stearate and divinylbenzene, methylmethacrylate and ethylene glycol dimethacrylate, or lauryl methacrylate and ethylene glycol dimethacrylate. Usually, the monoethylenically unsaturated monomer will be present at from about 20% to about 80% of the monomer mixture, with the polyethylenically unsaturated monomer forming the remainder of the mixture.

Resilient and compressible, as opposed to rigid, particles can be made by the use of curable elastomers. Examples of such elastomers are isoprene rubbers, butadiene rubbers, chloroprene rubbers, isobutylene-isoprene rubbers, nitrile-butadiene rubbers, styrene-butadiene rubbers, and ethylene-propylene-diene terpolymers.

Additional particles useful in the practice of this invention are those that contain cationic functionalities on the particle surface. These charged functionalities increase the substantivity of the particles, i.e., their affinity for keratin and thus the adherence of these particles to hair and skin and their resistance to being separated from hair and skin upon being rinsed with water.

Particles with cationic functionalities can be formed by polymerization of a cationic monomer, or by quaternizing or otherwise protonating surface functionalities on the polymer once the particle is formed. Examples of monomers that contain protonatable functionalities are vinyl pyridines such as 2-vinyl pyridine, 4-vinyl pyridine, 3-methyl-2-vinyl pyridine, 4-methyl-2-vinyl pyridine, 6-methyl-2-vinyl pyridine, 3-ethyl-2-vinyl pyridine, 5-ethyl-2-vinyl pyridine, 2-methyl-3-vinyl pyridine, 2-methyl-4-vinyl pyridine, 2-methyl-5-vinyl pyridine, and 2-ethyl-5-vinyl pyridine. Further examples are acrylates and methacrylates, such as methacrylamidopropylhydroxyethyldimethylammonium acetate, methacrylamidopropyltrimethylammonium chloride, and the quaternization products of dimethylaminoethylmethacrylate and dimethyl sulfate, diethylaminoethylacrylate and dimethyl sulfate, vinylbenzyl chloride and divinylbenzene, and vinylbenzene and ethylene glycol dimethacrylate. When quaternized monomers are used, a counter ion such as $Cl^-$, $F^-$, $Br^-$, $I^-$, or $CH_3OSO_3^-$ is most often incorporated into the structure.

Specific examples of cationic particles are those obtained by the copolymerization of 4-vinylpyridine and ethylene glycol dimethacrylate; 4-vinylpyridine, methyl methacrylate and ethylene glycol dimethacrylate; 4-vinylpyridine and divinylbenzene; 2-vinylpyridine and divinylbenzene; 2-vinylpyridine and ethylene glycol dimethacrylate; ethyl methyl vinylpyridine and divinylbenzene; ethyl methyl vinylpyridine and ethylene glycol dimethacrylate; dimethylaminoethyl methacrylate, methyl chloride salt, and N,N'-methylenebisacrylamide; and trimethylammoniumethylmethacrylic chloride and N,N'-methylenebisacrylamide.

The protonation of polymeric particles bearing potonatable functionalities can be performed either before or after entrapping the retinoid composition within the porous network. Protonation immediately after the formation of the particles can readily be achieved by an acid wash such as a 3% aqueous hydrochloride solution, followed by removal of excess acid. Alternatively, the particles can be protonated by a buffered rinse at pH 3. An example of such a rinse is a a mixture comprising 0.1N potassium hydrogen phthalate and 0.1N HCl in deionized water.

Further descriptions of particles of this type are found in published European Patent Application No. 89311772.1, publication no. 369741, publication date May 23, 1990, and its pending United States counterpart, patent application Ser. No. 08/245,307, filed May 17, 1994. The disclosures of these documents are incorporated herein by reference.

Regardless of the particular type of particle used, impregnation of the particles with the retinoid composition is readily accomplished by contact absorption. The retinoid composition can be dissolved in a solvent to form a solution which, in addition to facilitating absorption, can be used to control the amount impregnated, control viscosity, and control any other parameters that can affect the quality and ease of absorption. Examples of such solvents are liquid petrolatum, polysorbate ether, petroleum ether, alcohols (e.g., methanol, ethanol, propylene glycol and higher alcohols), aromatics (e.g., benzene and toluene), alkanes (e.g., pentane, hexane and heptane), ketones (e.g., acetone and methyl ethyl ketone), chlorinated hydrocarbons (e.g., chloroform, carbon tetrachloride, methylene chloride, and ethylene dichloride), and oils (e.g., isopropyl myristate, diisopropyl adipate, mineral oil, and silicone oils). After absorption of the solution, the solvent can be evaporated, or if desired, retained inside the pores with the retinoid composition.

The retinoid-containing particles can be incorporated in fluid or solid compositions for preparations of the type commonly used for skin treatment. These preparations include gels, creams, lotions, ointments, sprays, powders, oils, and sticks. Aqueous fluid compositions such as oil-in-water and water-in-oil emulsions, gels, creams, lotions, ointments and sprays, where the particles are dispersed in an aqueous medium, are preferred. Regardless of the formulation, however, the medium in which the particles are dispersed can contain additional ingredients for any of a variety of cosmetic, therapeutic or preventive effects. Such ingredients are well known to those skilled in the art.

When particles of any of the types described above are suspended in aqueous fluid media, the concentration of the retinoid compositions relative to the entire formulation is preferably from about 0.001% to about 20.0% by weight, and most preferably from about 0.01% to about 5.0%.

The following examples are offered as illustration.

EXAMPLE I

This example illustrates the preparation of porous microscopic particles of generally spherical shape (hereinafter referred to as "microspheres") containing retinol in liquid form inside the pores. The retinol used in these examples was a retinol blend obtained from Roche Vitamins and Fine Chemicals, Nutley, N.J., USA, and contained 45% retinol by weight, with Polysorbate 20 and BHT constituting the remainder.

An impregnating solution was prepared by dissolving the following in 100 g ethanol, with amounts shown in grams:

| | |
|---|---|
| propyl gallate | 0.023 |
| sodium salt of ethylenediamine tetraacetic acid | 0.023 |
| retinol blend | 48.5 |
| vitamin E acetate | 1.0 |
| vitamin C | 0.23 |

The solution was degassed with nitrogen, and mixed with 100 g of polymerized methyl methacrylate/ ethyleneglycoldimethacrylate having a weight average particle diameter of 20 microns, a surface area of 225 $m^2/g$, and a pore volume of 1.0 $cm^3/g$ (hereinafter referred to as "acrylate microspheres"). Once the solution was absorbed by the microspheres, the solvent was removed and the impregnated microspheres were stored in brown glass jars which were flushed with nitrogen prior to storage.

EXAMPLE II

This example further illustrates the preparation of porous microspheres containing retinol in liquid form inside the pores, this time using microspheres of a different composition. The microspheres were polymerized from dimethylaminoethylmethacrylate, methyl chloride salt, and methylene bis-acrylamide, and thereby cationic in character, having a weight average particle diameter of 8 microns (hereinafter referred to as "cationic microspheres").

The impregnating solution was prepared by dissolving the following in 100 g ethanol, with amounts shown in grams:

| | |
|---|---|
| propyl gallate | 0.023 |
| sodium salt of ethylenediamine tetraacetic acid | 0.023 |
| retinol blend | 50.0 |
| vitamin E acetate | 1.0 |
| vitamin C | 0.23 |

The impregnation procedure was the same as that of Example I.

EXAMPLE III

This is a further illustration of the preparation of retinol-impregnated porous microspheres, the microspheres in this case further containing melanin as an antioxidant.

Melanin, in the form of an aqueous solution containing 10% color-modified melanin (i.e., melanin oxidized to convert the color from black to light brown for cosmetic appeal) by weight, was added to acrylate microspheres of the same type as those of Example I, using 1 g of the melanin solution and 48.23 g of the dry (empty) microspheres. The combined ingredients were mixed, then washed with 0.2N HCl until the pH of the mixture was between 4.5 and 5.0. Water was then removed by vacuum drying.

Separately, a retinol impregnating solution was prepared by dissolving the following in 50 g of ethanol (weights given in grams):

| | |
|---|---|
| propyl gallate | 0.023 |
| sodium salt of ethylenediamine tetraacetic acid | 0.023 |
| retinol blend | 49.5 |
| vitimin E | 1.0 |
| vitamin C | 0.23 |

The resulting solution was mixed with the melanin-impregnated microspheres and the resulting mixture was rolled on a mill. The solvent was then removed by vacuum drying. The impregnated spheres were then flushed with dry nitrogen and stored in a brown glass jar.

EXAMPLE IV

This example illustrates the preparation of melanin- and retinol-impregnated microspheres, using the cationic microspheres of Example II prepared from dimethylaminoethylmethacrylate, methyl chloride salt, and methylene bis-acrylamide.

The aqueous melanin solution used in Example III (1 g) was added to 50 g of the cationic microspheres. The solution and microspheres were mixed on a roll mill and the solvent was removed by vacuum drying. The retinol solution was prepared separately as in Example III, and added to the melanin-containing cationic microspheres. The resulting mixture was roll milled and vacuum dried to remove the solvent. The resulting impregnated spheres were stored until further use in brown bottles that had been purged with nitrogen.

EXAMPLE V

This example illustrates the inclusion of retinol-impregnated microspheres in an oil-in-water formulation containing 0.6% retinol, and the effect of the formulation when used by volunteers upon applying it to their skin.

The components of the oil-in-water emulsion serving as the suspending medium were as follows, all figures given in parts by weight:

| | |
|---|---|
| deionized water | 75.8 |
| VEEGUM ® (magnesium aluminum silicate, R.T. Vanderbilt Co., Inc., Norwalk, Connecticut, USA) | 0.5 |
| glycerin | 3.0 |
| NATURECHEM ® (esters serving as emulsifying agents, CasChem Inc., Bayonne, New Jersey, USA) | 3.5 |
| Super Sterol Ester ($C_{10}$–$C_{30}$ cholesterol/-lanosterol esters, Croda Inc., Parsippany, New Jersey, USA) | 2.5 |
| stearic acid | 1.0 |
| cetyl alcohol | 3.0 |
| POLAWAX ® (emulsifying wax, Croda Inc., Parsippany, New Jersey, USA) | 4.0 |
| DOW CORNING ® 350 cst (silicone compound, Dow Corning Corp., Midland, Michigan, USA) | 2.0 |
| GENEROL ® 122 E-10 (soya sterol or ethoxylates, Henkel Corp., Ambler Pennsylvania, USA) | 0.5 |
| BHT | 0.06 |
| triethanolamine | 0.3 |

Impregnated microsponges as prepared in Example I, at 2.9 parts by weight, were suspended in this medium. The resulting suspension was applied by volunteers to their skin. The volunteers observed that the suspension produced very acceptable skin feel and aesthetics.

EXAMPLE VI

This example further illustrates the inclusion of retinol-impregnated microspheres in an oil-in-water emulsion similar to that of Example V, except with 0.15% retinol rather than 0.6%.

The emulsion serving as the suspending medium in parts by weight was as follows:

| | |
|---|---|
| deionized water | 77.0 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| GENEROL ® 122 E-10 | 0.5 |
| BHT | 0.06 |
| triethanolamine | 0.3 |
| GERMABEN ® (diazolydinyl urea blends, Sutton Laboratories, Inc., Chatham, New Jersey USA) | 1.0 |

Impregnated microsponges as prepared in Example I, at 0.80 parts by weight, were suspended in this medium.

EXAMPLE VII

This is a further illustration of the inclusion of retinol-impregnated microspheres in an oil-in-water emulsion. The formulation is similar to that of Example V, except with 0.3% retinol rather than 0.6%.

The emulsion serving as the suspending medium was as follows, in parts by weight:

| | |
|---|---|
| deionized water | 79.0 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| GENEROL ® 122 E-10 | 0.5 |
| BHT | 0.06 |
| triethanolamine | 0.3 |
| GERMABEN ® (diazolydinyl urea blends, Sutton Laboratories, Inc., Chatham, New Jersey USA) | 1.0 |

Impregnated microsponges as prepared in Example I, at 1.6 parts by weight, were suspended in this emulsion.

EXAMPLE VIII

This is a further illustration of the inclusion of retinol-impregnated microspheres in an oil-in-water emulsion. The formulation is similar to that of Example V, except that it contains 0.075% retinol.

The emulsion serving as the suspending medium in parts by weight was as follows:

| | |
|---|---|
| deionized water | 80.6 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| GENEROL ® 122 E-10 | 0.5 |
| BHT | 0.06 |
| triethanolamine | 0.3 |
| GERMABEN ® | 1.0 |

Impregnated microsponges as prepared in Example I, at 0.33 parts by weight, were suspended in this medium.

EXAMPLE IX

As a still further illustration of the use of retinol-impregnated microspheres in an oil-in-water emulsion. A 1% retinol formulation was prepared, using the following emsulion as the suspending medium, in parts by weight:

| | |
|---|---|
| deionized water | 78.84 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| GENEROL ® 122 E-10 | 0.5 |
| BHT | 0.06 |
| triethanolamine | 0.3 |
| GERMABEN ® | 1.0 |

Impregnated microsponges as prepared in Example I, at 4.8 parts by weight, were suspended in this medium.

EXAMPLE X

This example illustrates the impregnation of microspheres with both retinol and melanin, using black melanin and acrylate spheres. The procedure of Example III was repeated, except that black melanin was substituted for the color-modified melanin used in Example III.

EXAMPLE XI

This example illustrates the use of retinol- and melanin-impregnated acrylate microspheres to form another particle suspension.

A suspending medium was prepared as follows (in parts by weight):

| | |
|---|---|
| deionized water | 78.5 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| GENEROL ® 122 E-10 | 0.5 |
| BHT | 0.06 |
| triethanolamine | 0.3 |

Acrylate microspheres impregnated with melanin and retinol according to the procedure of Example III, at 2.4 parts by weight, were suspended in this medium.

EXAMPLE XII

This example illustrates the use of retinol- and melanin-impregnated cationic microspheres to form a particle suspension formulation.

An oil-in-water emulsion to serve as the suspending medium was prepared as follows (in parts by weight):

| | |
|---|---|
| deionized water | 79.5 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohol | 3.0 |
| POLAWAX ® | 4.0 |
| DOW CORNING ® 350 cst | 2.0 |
| BHT | 0.06 |
| triethanolamine | 0.3 |
| GERMABEN ® | 1.0 |

Microspheres made from dimethylaminoethylmethacrylate, methyl chloride salt, and methylene bis-acrylamide were impregnated with melanin and retinol, as in Example IV, at 2.41 parts by weight, and then suspended in this emulsion.

EXAMPLE XIII

This example illustrates the inclusion of retinol-impregnated microspheres inan oil-in-water emulsion to form a formulation containing 0.6% retinol, similar to Example V except that cationic microspheres were used.

The oil-in-water emulsion serving as the suspending medium was as follows (in parts by weight):

| | |
|---|---|
| deionized water | 75.8 |
| VEEGUM ® | 0.5 |
| glycerin | 3.0 |
| NATURECHEM ® | 3.5 |
| Super Sterol Ester | 2.5 |
| stearic acid | 1.0 |
| cetyl alcohoi | 3.0 |
| POLAWAX ® | 4.0 |
| DOW CORNING ® 350 cst | 2.0 |
| GENEROL ® 122 E-10 | 0.5 |
| BHT | 0.3 |
| triethanolamine | 0.3 |

Microspheres made from dimethylaminoethylmethacrylate, methyl chloride salt, and methylene bis-acrylamide and impregnated with retinol, as prepared in Example II, at 2.9 parts by weight, were suspended in this medium.

EXAMPLE XIV

This example reports the results of accelerated aging tests for retinol stability determinations in acrylate microsphere preparations of retinol suspended in oil-in-water emulsions.

Five particle suspensions were prepared as described in Examples V through IX above, and each was subjected to a prolonged thermal treatment at 45° C. to accelerate aging. The retinol contents ranged from 0.15% by weight to 0.6% by weight. The formulations were placed in opaque plastic jars, glaminate and aluminum tubes. All containers were sealed and placed in an incubator at 45° C. Samples were taken from various containers and analyzed for retinol by high pressure liquid chromatography (HPLC), at the beginning of the experiment and at 2 weeks, 6 weeks and 12 weeks. The results are reported in Table I below.

TABLE I

Accelerated Aging Test Results

| Formulation as Prepared (test vessel) | Weight Percent Retinol Remaining | | | |
|---|---|---|---|---|
| | Start of Test | 2 Weeks | 6 Weeks | 12 Weeks |
| 0.6% Retinol (jar) | 0.61 | — | — | 0.56 |
| 0.5% Retinol (tube) | 0.50 | — | 0.47 | 0.45 |
| 0.6% Retinol (tube) | 0.60 | — | 0.56 | — |
| 0.15% Retinol (tube) | 0.15 | 0.15 | — | — |
| 0.33% Retinol (tube) | 0.33 | 0.33 | — | — |

The data in this table indicate that in all cases at least 90% of the retinol remains after accelerated aging at 45° C. This level of stability is acceptable for a commercial product.

EXAMPLE XV

This example presents the results of skin irritation tests obtained with a particle suspension prepared as described in Examples I through V above with the following concentrations of retinol as retained by the microspheres—0.3%, 0.5%, 0.75%, and 1% (all by weight). For comparison, a particle suspension lacking retinol but otherwise identical to the 0.3% retinol particle suspension was used as a placebo. A water-in-oil formulation lacking the microspheres but containing the 0.3% retinol was used for further comparison, and a 0.2% aqueous sodium lauryl sulfate solution was used for still further comparison.

The water-in-oil formulation containing 0.3% retinol consisted of the following ingredients, in parts by weight:

| | |
|---|---|
| squalane | 1.0 |
| glycerin | 6.0 |
| pentaerythritol tetraoctanoate | 1.0 |
| butylene glycerol | 2.0 |
| petroleum jelly | 73.0 |
| BENTONE ® (hydrous magnesium aluminum silicate, Rheox, Inc., Hightstown, New Jersey, USA) | 2.0 |
| glyceryl stearate | 4.0 |
| polyglycerol | 3.0 |
| retinol | 0.3 |
| vitamin E acetate | 0.5 |
| sodium citrate | 0.3 |
| ethylenediamine tetraacetic acid | 0.2 |
| parahydroxybenzoate | 0.5 |
| BHT | 0.2 |

The skin irritation test was conducted on thirty subjects. Occlusive patching devices were affixed to intact skin sites on the backs of the subjects, each subject bearing one occlusive patching device for each of the test formulations. The webbed pad of each patching device was coated with approximately 100 mg of formulation, and the study regimen consisted of fourteen consecutive daily applications each of 24 hours' duration, and each followed by an examination of the test sites for adverse effects. The results were assigned scores as follows:

| Description | Score |
|---|---|
| Erythema Stage: | |
| faint redness | 1 |
| moderate redness | 2 |
| intense redness | 3 |
| Infiltration Phase: | |
| redness plus edema and/or papules | 4 |
| redness plus vesicles, blisters or bullae | 5 |
| redness plus extension of effect beyond margin of contact site | 6 |
| Absence of both Erythema Stage and Infiltration Stage | 0 |

The results are shown in Table II below, where each irritation score represents an average over all thirty subjects.

TABLE II

Skin Test Results

| Form | Retinol Content (weight percent) | Irritation Score |
|---|---|---|
| Impregnated microsphere suspension in oil-in-water emulsion | 0.3 | 1.24 |
| Impregnated microsphere suspension in oil-in-water emulsion | 0.5 | 1.76 |
| Impregnated microsphere suspension in oil-in-water emulsion | 0.75 | 1.93 |
| Impregnated microsphere suspension in oil-in-water emulsion | 1.0 | 2.17 |
| Impregnated microsphere suspension in oil-in-water emulsion | 0 | 0.17 |
| 0.2% Aqueous sodium lauryl sulfate solution (no microspheres) | 0 | 4.79 |
| Water-in-oil emulsion (no microspheres) | 0.3 | 2.04 |

The data in Table II indicate that the 0.3% water-in-oil formulation is more irritating than the 0.3% retinol microsphere emulsion. The data further shows that the 0.3% retinol water-in-oil formulation is more irritating than the 0.5% and 0.75% retinol microsphere suspensions.

The foregoing is offered primarily for purposes of illustration. It will be readily apparent to those skilled in the art that the components, proportions, formulating ingredients, methods of formulation, and methods of administration described herein may be further modified or substituted in various ways without departing from the spirit and scope of the invention.

We claim:

1. A stable pharmaceutical composition for topical administration of retinol consisting of an oil-in-water emulsion comprising, suspended in the emulsion, solid water-insoluble microscopic particles containing a substantially continuous network of pores open to the exterior of the particles and a retinoid composition comprising retinol residing only in the pores, the composition causing lower irritancy when applied than a composition containing the same concentration of retinol in a non-(microscopic particle) formulation.

2. A stable pharmaceutical composition for topical administration of retinol consisting of an oil-in-water emulsion comprising, suspended in the emulsion, solid water-insoluble microscopic particles containing a substantially continuous network of pores open to the exterior of the particles and a retinoid composition comprising retinol residing only in the pores, the concentration of the retinoid composition relative to the pharmaceutical composition being between about 0.001% and about 20.0% by weight, the composition causing lower irritancy when applied than a composition containing the same concentration of retinol in a non-(microscopic particle) formulation.

3. The pharmaceutical composition of claim 2 where the concentration of the retinoid composition relative to the pharmaceutical composition is between about 0.01% and about 5.0% by weight.

4. The pharmaceutical composition of claim 3 where the retinoid composition contains from about 1% to about 90% by weight of retinol.

5. The composition of claim 4 where the retinoid composition contains from about 5% to about 60% by weight of retinol.

6. The composition of claim 5 where the retinoid composition further contains from about 0.01% to 1% by weight of a chelating agent.

7. The composition of claim 6 where the retinoid composition further contains from about 10% to about 75% by weight of an antioxidant.

8. The composition of claim 7 where the retinoid composition further contains a surfactant.

9. A stable pharmaceutical composition for topical administration of retinol consisting of an oil-in-water emulsion comprising, suspended in the emulsion, solid water-insoluble microscopic particles containing a substantially continuous network of pores open to the exterior of the particles and a retinoid composition comprising from about 5% to about 60% by weight of retinol, from about 10% to about 75% by weight of an antioxidant, from about 0.01% to about 1% by weight of a chelating agent, and a surfactant, residing only in the pores, the concentration of the retinoid composition relative to the pharmaceutical composition being between about 0.01% and about 5.0% by weight, the composition causing lower irritancy when applied than a composition containing the same concentration of retinol in a non-(microscopic particle) formulation.

10. The composition of claim 9 where the oil-in-water emulsion comprises, by weight, about 75% to about 81% water, 0.5% magnesium aluminum silicate, 3.0% glycerin, 3.5% emulsifying esters, 2.5% cholesterol/lanosterol esters, 1.0% stearic acid, 3.0% cetyl alcohol, 4.0% emulsifying wax, 2.0% silicone fluid, 0.5% soya sterol ethoxylates, 0.3% triethanolamine, 0.06–0.3% BHT, and 0–1.0% diazolidinylurea.

11. The composition of claim 1 where the solid particles are formed of a crosslinked polymer.

12. The composition of claim 11 where the crosslinked polymer is selected from a copolymer of styrene and divinylbenzene, a copolymer of vinyl stearate and divinylbenzene, a copolymer of methyl methacrylate and ethylene glycol dimethacrylate, and a copolymer of lauryl methacrylate and ethylene glycol dimethacrylate.

13. The composition of claim 2 where the solid particles are formed of a crosslinked polymer.

14. The composition of claim 13 where the crosslinked polymer is selected from a copolymer of styrene and divinylbenzene, a copolymer of vinyl stearate and divinylbenzene, a copolymer of methyl methacrylate and ethylene glycol dimethacrylate, and a copolymer of lauryl methacrylate and ethylene glycol dimethacrylate.

15. The composition of claim 9 where the solid particles are formed of a crosslinked polymer.

16. The composition of claim 15 where the crosslinked polymer is selected from a copolymer of styrene and divinylbenzene, a copolymer of vinyl stearate and divinylbenzene, a copolymer of methyl methacrylate and ethylene glycol dimethacrylate, and a copolymer of lauryl methacrylate and ethylene glycol dimethacrylate.

* * * * *

UNITED STATES PATENT AND TRADEMARK OFFICE
CERTIFICATE OF CORRECTION

PATENT NO.    : 5,851,538
DATED         : Dec. 22, 1998
INVENTOR(S)   : Froix et al.

It is certified that error appears in the above-indentified patent and that said Letters Patent is hereby corrected as shown below:

On the title page;

-- [75] Inventors:    Michael Froix, Mountain View; Masha Pukshansky, San Francisco; Sergio Nacht, Redwood City; Subhash J. Saxena; Belmont; Sandhya Singh, San Jose, all of Calif. --

Signed and Sealed this

Sixteenth Day of November, 1999

Attest:

Q. TODD DICKINSON

*Attesting Officer*     *Acting Commissioner of Patents and Trademarks*